(12) United States Patent
Pinchuk

(10) Patent No.: US 11,517,476 B2
(45) Date of Patent: Dec. 6, 2022

(54) SYSTEMS, METHODS, AND APPARATUS FOR TREATMENT OF GLAUCOMA

(71) Applicant: InnFocus, Inc., Miami, FL (US)

(72) Inventor: Leonard Pinchuk, Miami, FL (US)

(73) Assignee: InnFocus, Inc., Miami, FL (US)

( * ) Notice: Subject to any disclaimer, the term of this patent is extended or adjusted under 35 U.S.C. 154(b) by 179 days.

(21) Appl. No.: 16/621,079

(22) PCT Filed: May 24, 2018

(86) PCT No.: PCT/US2018/034301
§ 371 (c)(1),
(2) Date: Dec. 10, 2019

(87) PCT Pub. No.: WO2018/231485
PCT Pub. Date: Dec. 20, 2018

(65) Prior Publication Data
US 2020/0188172 A1      Jun. 18, 2020

Related U.S. Application Data

(60) Provisional application No. 62/518,944, filed on Jun. 13, 2017.

(51) Int. Cl.
*A61F 9/007*      (2006.01)
(52) U.S. Cl.
CPC ............................... *A61F 9/00781* (2013.01)
(58) Field of Classification Search
CPC .......... A61F 9/00781; A61F 2250/0013; A61F 2250/0069; A61F 2250/0067
See application file for complete search history.

(56) References Cited

U.S. PATENT DOCUMENTS 4,521,210 A * 6/1985 Wong .................. A61F 9/00781
623/905
4,897,255 A 1/1990 Fritzberg et al.
(Continued)

FOREIGN PATENT DOCUMENTS

CH       700142 A1    6/2010
CN       2287027 Y    8/1998
(Continued)

OTHER PUBLICATIONS

Instructions for Use for Cypass System, dated Jul. 26, 2016, downloaded from https://www.accessdata.fda.gov/cdrh_docs/pdf15/P150037D.pdf.
(Continued)

*Primary Examiner* — Philip R Wiest
*Assistant Examiner* — Alessandro R Del Priore
(74) *Attorney, Agent, or Firm* — Gordon & Jacobson, P.C.

(57) ABSTRACT

A glaucoma drainage device includes an elongated body extending axially from a distal end to a proximal end. The distal end forms a wedge with a leading distal edge. During implantation of the device into the suprachoroidal space of the eye, the wedge can facilitate penetration into and spreading open the tissue of the suprachoroidal space. The elongate body has one or more outer surfaces that define at least one open groove extending from at or near the proximal end towards the distal end of the body. With the distal end of the elongate body located in the suprachoroidal space of the eye and the distal end of the elongate body extending into the anterior chamber of the eye, the at least one open groove is configured such that aqueous humor flows along the open groove from the anterior chamber of the eye to the suprachoroidal space of the eye.

16 Claims, 5 Drawing Sheets

(56) References Cited

U.S. PATENT DOCUMENTS

| | | | |
|---|---|---|---|
| 5,601,094 A * | 2/1997 | Reiss | A61F 9/00781 604/8 |
| 5,879,319 A * | 3/1999 | Pynson | A61F 9/00781 604/8 |
| 7,431,709 B2 | 10/2008 | Pinchuk et al. | |
| 7,594,899 B2 | 9/2009 | Pinchuk et al. | |
| 7,708,711 B2 * | 5/2010 | Tu | A61M 27/002 604/9 |
| 7,837,644 B2 | 11/2010 | Pinchuk et al. | |
| 7,862,531 B2 | 1/2011 | Yaron et al. | |
| 7,909,789 B2 | 3/2011 | Badawi et al. | |
| 8,034,016 B2 * | 10/2011 | Yaron | A61F 9/00781 604/9 |
| 8,685,435 B2 | 4/2014 | Nivaggioli et al. | |
| 8,911,496 B2 * | 12/2014 | Jacobson | A61B 17/083 623/4.1 |
| 9,011,361 B2 | 4/2015 | deJuan, Jr. et al. | |
| 9,044,301 B1 | 6/2015 | Pinchuk et al. | |
| 9,101,444 B2 | 8/2015 | Pinchuk | |
| 9,480,598 B2 * | 11/2016 | Clauson | A61F 9/00781 |
| 9,561,132 B2 | 2/2017 | Stegman et al. | |
| 9,649,223 B2 | 5/2017 | Pinchuk | |
| 2005/0119601 A9 * | 6/2005 | Lynch | A61F 9/00781 600/398 |
| 2007/0123812 A1 * | 5/2007 | Pinchuk | A61F 9/00781 604/8 |
| 2007/0191863 A1 | 8/2007 | De Juan, Jr. et al. | |
| 2008/0228127 A1 | 9/2008 | Burns et al. | |
| 2009/0221992 A1 * | 9/2009 | Hannon | A61M 25/1002 604/544 |
| 2010/0010416 A1 | 1/2010 | Juan, Jr. et al. | |
| 2010/0274259 A1 | 10/2010 | Yaron et al. | |
| 2011/0028983 A1 | 2/2011 | Silvestrini et al. | |
| 2012/0245505 A1 | 9/2012 | Robinson et al. | |
| 2013/0131577 A1 | 5/2013 | Bronstein et al. | |
| 2013/0165840 A1 | 6/2013 | Orge | |
| 2014/0081195 A1 | 3/2014 | Clauson et al. | |
| 2016/0135992 A1 | 5/2016 | Schaller et al. | |

FOREIGN PATENT DOCUMENTS

| | | |
|---|---|---|
| CN | 101199440 A | 6/2008 |
| CN | 201216683 Y | 4/2009 |
| CN | 103181842 A | 7/2013 |
| CN | 104490515 A | 4/2015 |
| CN | 104984420 A | 10/2015 |
| CN | 105434103 A | 3/2016 |
| CN | 105899170 A | 8/2016 |
| WO | 2007/087061 A2 | 8/2007 |
| WO | 2014/151070 A1 | 9/2014 |

OTHER PUBLICATIONS

Search Report and Written Opinion dated 2018-18-28 of Application No. PCT/US 18/34301.
Taiwan Office Action and Search Report dated Aug. 9, 2021 of Application No. 107119574.
Supplemental EP Search Report dated Feb. 8, 2021 of Application No. EP18 81 8723.
Chinese Office Action dated Aug. 2, 2021 of Application No. 201880039591.X.
Chinese Search Report dated Jul. 23, 2021 of Application No. 201880039591.X.
Chinese Office Action dated Mar. 1, 2022 of Application No. 201880039591.X.
Chinese Supplemental Search Report dated Feb. 21, 2022 of Application No. 201880039591.X.
Japanese Office Action dated May 26, 2022 of Application No. 2019-568712.
Chinese Office Action dated Jul. 26, 2022 of Application No. 201880039591.X.
Chinese Supplemental Search Report dated Jul. 13, 2022 of Application No. 201880039591.X.

* cited by examiner

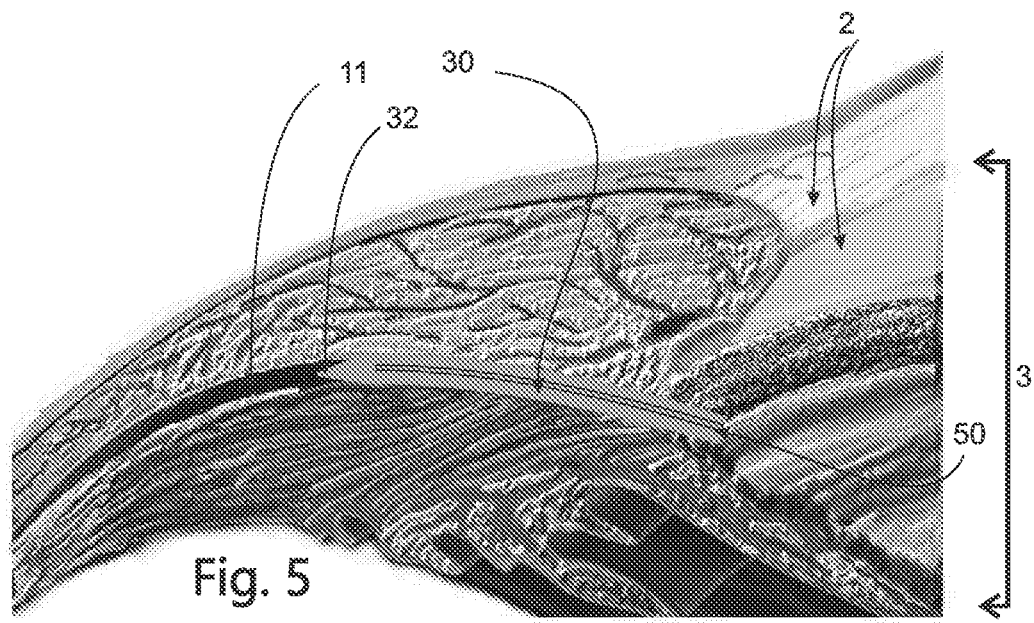
Fig. 5
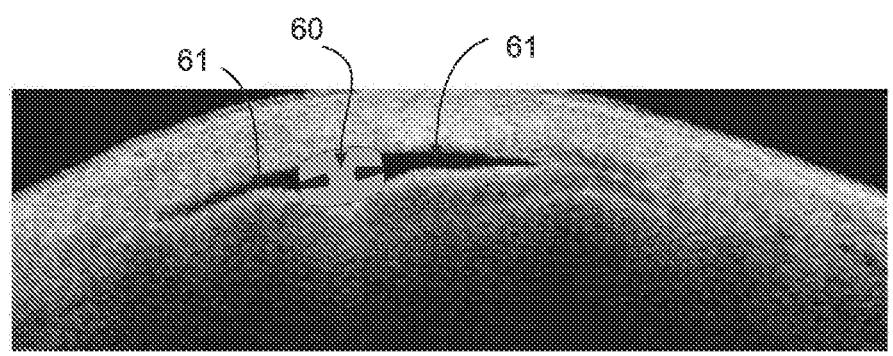
Fig. 6
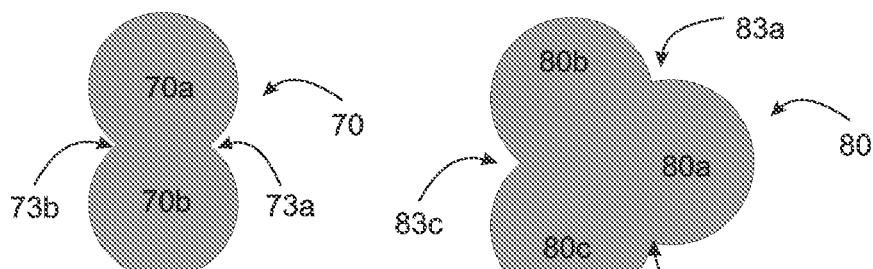
Fig. 7
Fig. 8

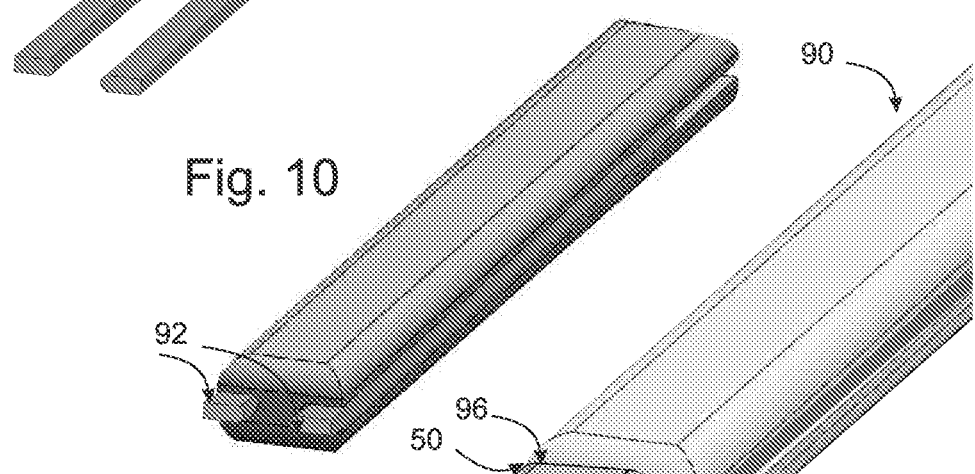
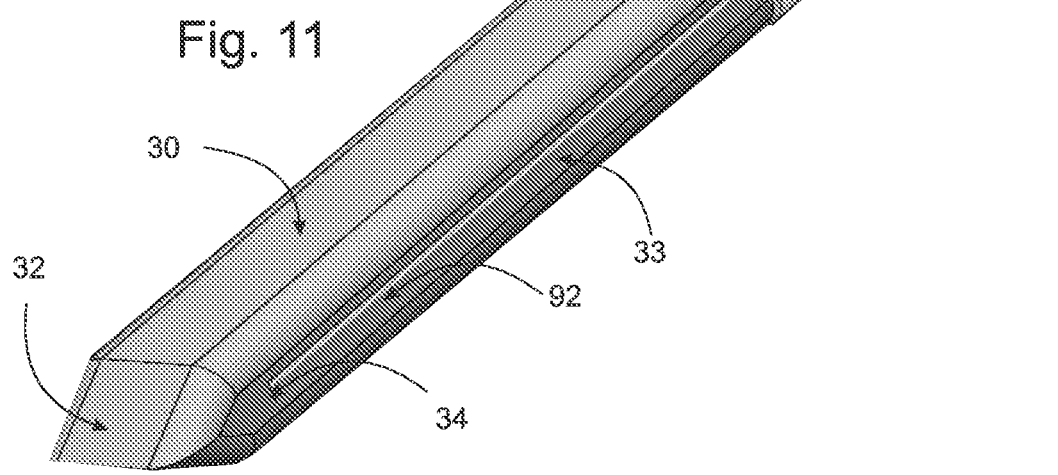

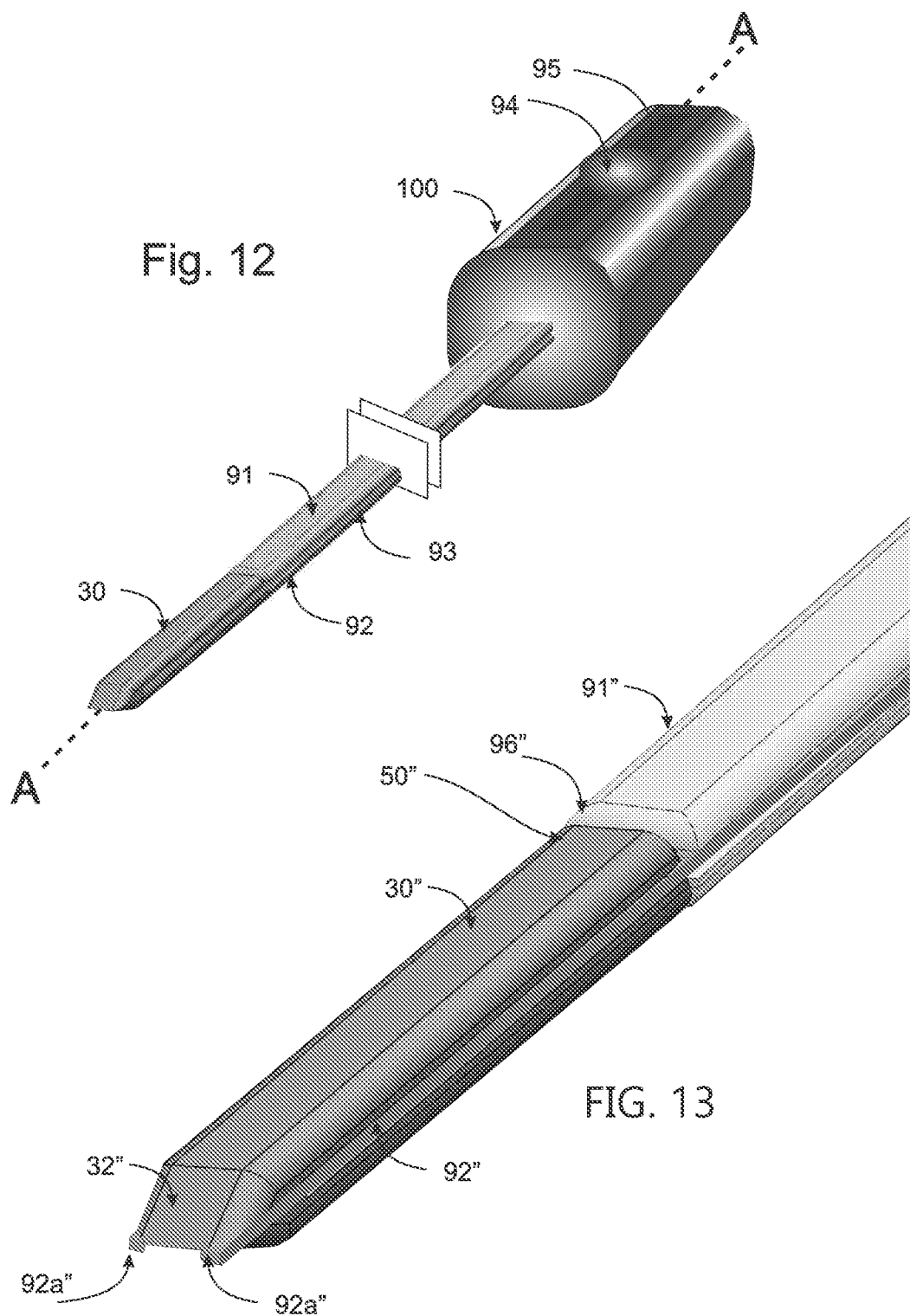

SYSTEMS, METHODS, AND APPARATUS FOR TREATMENT OF GLAUCOMA

CROSS-REFERENCE TO RELATED APPLICATION

This application claims priority to U.S. Provisional Patent Application No. 62/518,944 filed Jun. 13, 2017, the entire contents of which are incorporated herein by reference.

BACKGROUND

1. Field

The present disclosure relates to the treatment of glaucoma, and more particularly, to medical devices and methods for creating a drainage pathway to divert aqueous humor out of the anterior chamber of the eye such that pressure within the eye is reduced.

2. State of the Art

Aqueous humor is produced by the eye's ciliary body and flows from the ciliary body into the anterior chamber, out through a spongy tissue at the front of the eye called the trabecular meshwork and into a drainage canal. In a healthy eye, continuous drainage of aqueous humor keeps intraocular pressure at a normal level. However, in most types of glaucoma, proper circulation of aqueous humor is disrupted, causing the level of intraocular pressure to be elevated. In open-angle glaucoma, fluid does not flow freely through the trabecular meshwork, causing an increase in intraocular pressure, damage to the optic nerve and vision loss. Reduction of intraocular pressure is a means of stopping the progression of optic nerve damage, which if untreated can lead to blindness.

The suprachoroidal space is a space in the eye that lies between the sclera and the choroid. It is known that aqueous humor in the suprachoroidal space can drain therefrom and cause a reduction in intraocular pressure. Although it is not well understood where aqueous humor drains to once it reaches the suprachoroidal space, there are references to aqueous humor draining into the choroid vessels as well as into the venous plexus of the sclera and to the episcleral veins.

Alcon Laboratories, Inc. of Fort Worth, Tex. has developed the CyPass® Microstent that includes a tubular body with an internal lumen that drains aqueous humor from the anterior chamber of the eye into the suprachoroidal space of the eye to lower intraocular pressure in the eye.

SUMMARY

Widening the space between the choroid and the sclera (suprachoroidal space or supraciliary space) enables aqueous humor to enter the suprachoroidal space and drain therefrom through an alternate drainage pathway of the eye and reduce intraocular pressure. The terms "suprachoroidal space" and "supraciliary space" refer to the same space in the eye and those two terms, therefore, are interchangeable. According to one aspect of the disclosure, a device is provided for implantation into the suprachoroidal space of the eye to promote drainage of aqueous humor from the anterior chamber of the eye to the suprachoroidal space of the eye in order to reduce intraocular pressure. The device may be made from a flexible, bio-inert, and biocompatible material that can be inserted into the suprachoroidal space of the eye using an ab interno approach, conform to the curvature of the tissue surrounding the suprachoroidal space (i.e., the sclera and the choroid), and remain in place for a long period of time.

According to one aspect, further details of which are described herein, the device includes an elongated body extending axially from a distal end to a proximal end. The distal end of elongate body forms a wedge with a leading distal edge. During implantation of the device into the suprachoroidal space of the eye, the wedge with leading distal edge can facilitate penetration into and spreading open the tissue of the suprachoroidal space of the eye. The elongate body has one or more outer surfaces that define at least one open groove extending from at or near the proximal end towards the distal end of the body. With the distal end of the elongate body located in the suprachoroidal space of the eye and the distal end of the elongate body extending into the anterior chamber of the eye, the at least one open groove is configured such that aqueous humor flows along the open groove from the anterior chamber of the eye to the suprachoroidal space of the eye. Due to the open nature of the open groove, the flow path of the aqueous humor that flows along the open groove can be bounded by ocular tissue disposed adjacent the open groove along the length of the open groove.

In embodiment(s), the body of the device defines an abutment at a distal end of the at least one open groove. Also, in embodiment(s), the body has an upper outer surface and a lower outer surface that are substantially planar in form. In one embodiment, barbs extend from the upper and lower surfaces. The barbs may be tapered to permit insertion in one direction and resist removal in an opposite direction.

In embodiment(s), the device is formed from a soft flexible polymeric material. Examples of such soft flexible polymeric material includes poly(styrene-block-isobutylene-block-styrene) (SIBS), styrene ethylene butylene styrene (SEBS), polyhexene, polypropylene, polyethylene, and combinations thereof. The material may have a hardness of Shore 30A to 60A.

According to another aspect, further details of which are described herein, a system includes the device and an inserter coupled to the device. The inserter is configured to hold the device while positioning the distal end of the device in the suprachoroidal space and to decouple from the device to deploy the device in a desired location in the suprachoroidal space. The inserter may include a handle and at least one rigid member configured for longitudinal translation relative to the handle. Each rigid member is configured for longitudinal translation in a corresponding open groove of the device. The inserter holds the device with each rigid member in an extended configuration in which the rigid member extends along at least a portion of the corresponding open groove of the device. In embodiment(s), the inserter is configured to decouple from the device by reconfiguring each rigid member from the extended configuration to a retracted configuration in which the rigid member is removed from the open groove of the device.

As used herein, "rigid" means that the inserter will not bend or buckle under a range of forces (e.g., axial and radial compressive forces) that may be imparted to the inserter by the hand of the user when the inserter is introduced into the eye, as described in greater detail below. Also, as used herein, "flexible" means that the device, if unsupported by the inserter, will bend or buckle under the axial and radial compressive forces that may be imparted to the inserter during its use.

In embodiment(s), the at least one rod is coupled to a slide member configured for actuation by a user's hand. The inserter handle defines a longitudinal slot extending axially along the length of the handle and parallel with the at least one rod, and the slide member is configured to slide within the slot to move the rod between the extended and retracted configurations.

According to yet another aspect, further details of which are described herein, a method of implanting the device includes providing the device coupled to the inserter, introducing the device into the eye while maintaining the handle outside of the eye, positioning the device at a desired implanted position in the suprachoroidal space, and, with the device positioned at the desired implanted position, decoupling the inserter from the device. In embodiment(s) positioning the device at a desired implanted position in the suprachoroidal space includes positioning the distal end of the device in the suprachoroidal space and positioning the proximal end of the device in the anterior chamber. At the desired position, the device may extend about 0.5 mm to 1 mm into the anterior chamber.

BRIEF DESCRIPTION OF THE DRAWINGS

FIGS. 5 and 6 show the glaucoma drainage device of FIGS. 3A and 3B in an implanted configuration.

FIGS. 7 and 8 show alternative cross sections, respectively, of two other embodiments of glaucoma drainage device in accordance with this disclosure.

FIG. 9 shows a portion of an embodiment of a deployment tool in an extended configuration.

FIG. 10 shows the portion of the deployment tool of FIG. 9 in a retracted configuration.

FIG. 11 shows the portion of the deployment tool of FIG. 9 in the extended configuration coupled to the glaucoma drainage device of FIGS. 3A and 3B.

FIG. 12 shows the deployment tool of FIGS. 9 to 11 with its handle coupled to the glaucoma drainage device of FIGS. 3A and 3B.

FIG. 13 shows an alternative embodiment of the deployment tool of FIGS. 9 to 12 and alternative embodiment of the glaucoma drainage device of FIGS. 3A and 3B.

DETAILED DESCRIPTION

Figure 1:
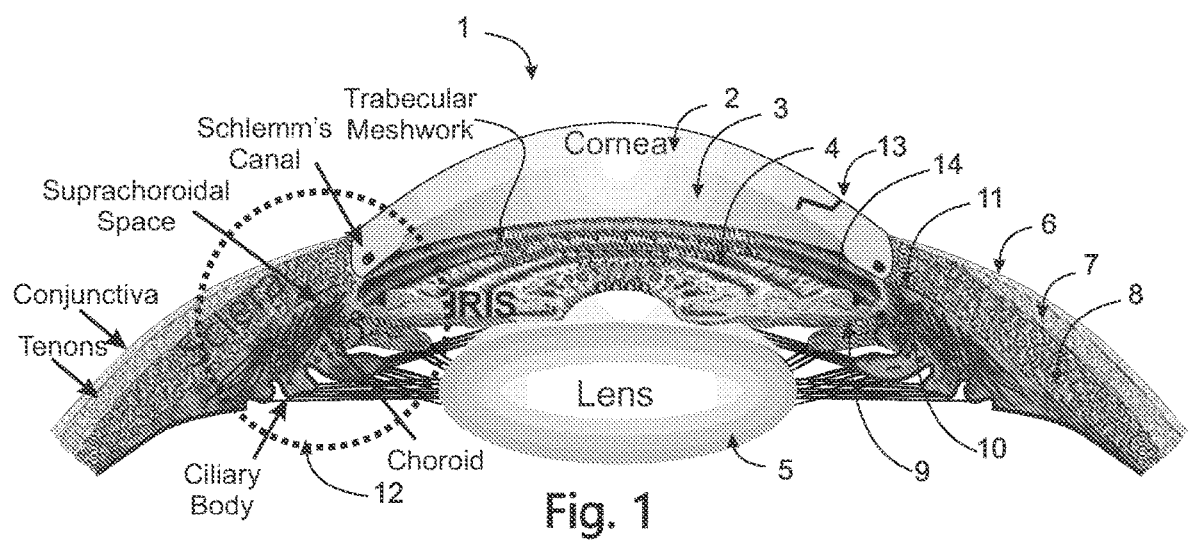
FIG. 1 is a section view of an anterior segment of an eye.

FIG. 1 shows details of an anterior segment of an eye. An anterior segment of an eye 1 includes a cornea 2, anterior chamber 3, iris 4, lens 5, conjunctiva 6, Tenon's Capsule 7, sclera 8, ciliary muscle 9, choroid 10, and suprachoroidal space 11. The suprachoroidal space 11 is bounded between the choroid 10 and the sclera 8. The choroid 10 contains blood vessels that interpenetrate the upper part of the ciliary body 9. Those blood vessels become more organized into a more distinct layer more posterior to the anterior chamber 3. A clear corneal incision 13, or a precisely articulated incision used in the cornea 2, is used to access the anterior chamber 3 during ab interno anterior segment surgery such as cataract surgery. Clear corneal incision 13 can be made with a scalpel or with a laser. The anterior chamber 3 is typically filled with a visco-elastic material during cataract surgery and procedures of this nature.

Figure 2:
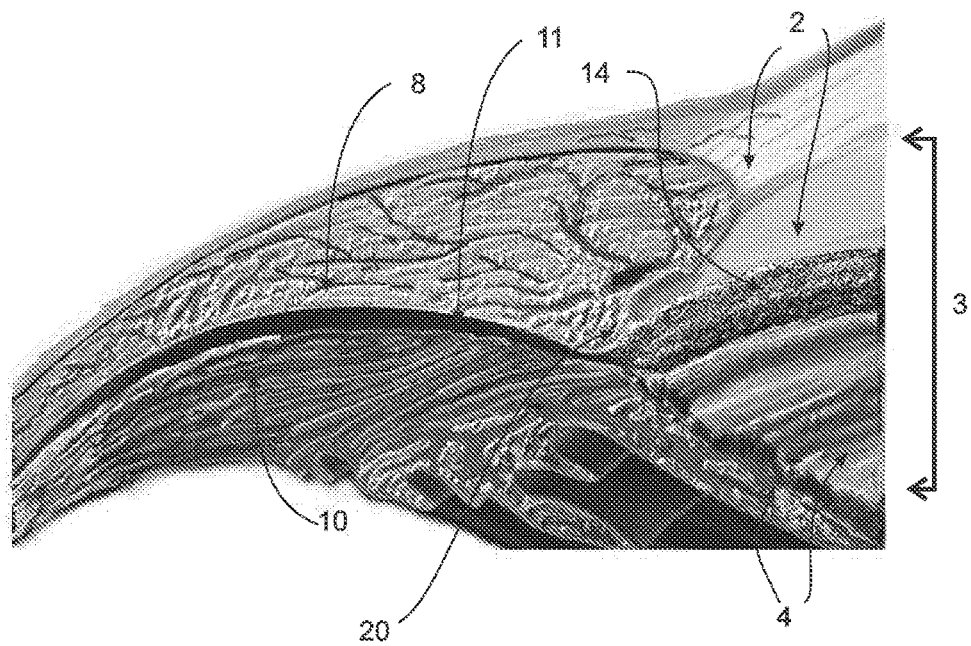
FIG. 2 is an exploded view of the portion of FIG. 1 surrounded by the dotted circle.

Dotted circle 12 denotes a portion of interest to this disclosure and is shown in greater detail in FIG. 2. The suprachoroidal space 11 is situated just below a scleral spur 20. A surgeon looking through a gonio lens (not shown) into the anterior chamber 3 through the cornea 2 can readily identify the scleral spur 20 and the entrance to the suprachoroidal space 11.

Figures 3A, 3B:
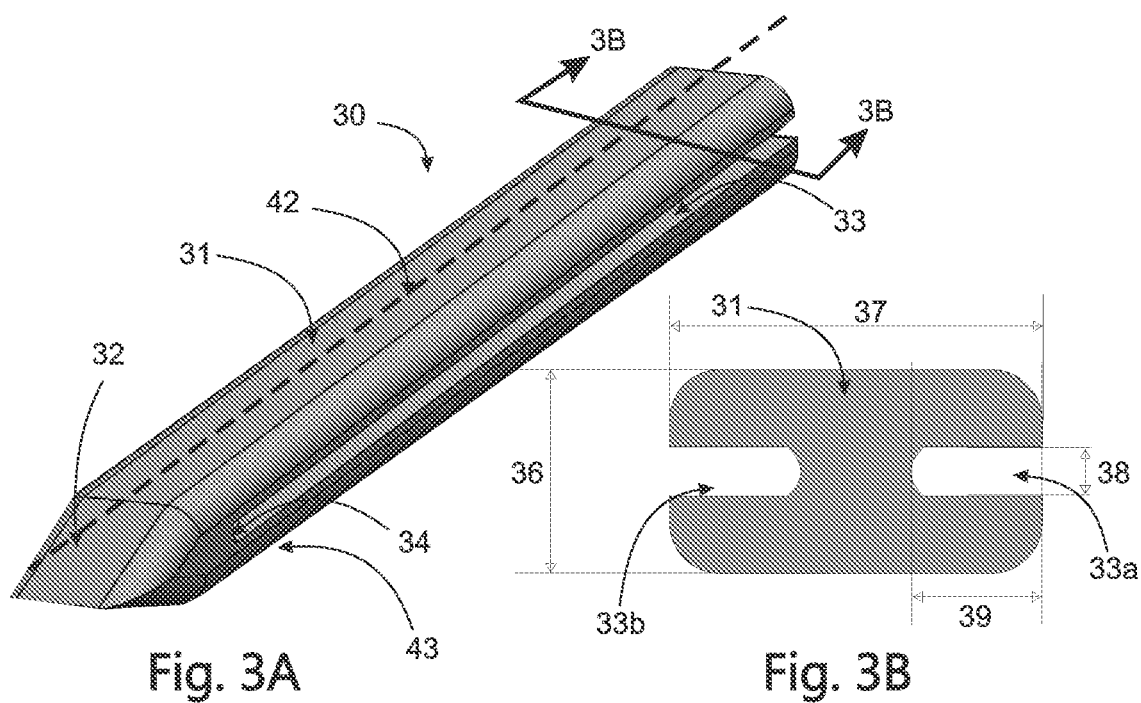
FIG. 3A is an isometric view of an embodiment of a glaucoma drainage device in accordance with this disclosure.
FIG. 3B is a section view of the glaucoma drainage device of FIG. 3A viewed along section 3B-3B in FIG. 3A.

FIG. 3A shows an embodiment of a glaucoma drainage device 30, hereinafter referred to as a "wedge", that is configured for insertion into the suprachoroidal space 11, as shown in FIG. 5, for example, and described in greater detail below. In the embodiment shown, the wedge 30 is comprised of an elongated body 31, hereinafter referred to as a "rod", which is shown as being a filleted rectangular (rectangular in terms of the overall planform) rod with a tapered distal end 32. The rod 31 has outer surfaces 42 (top surface) and 43 (bottom surface) that define at least one open groove or channel 33 extending from at or near a proximal end 50 towards the distal end 32. The groove or channel 33 extends parallel to the longitudinal axis A-A. The upper surface 42 and lower surface 43, are planar when the wedge 30 is laid on a flat surface and not subject to external forces. Of course, the open groove or channel 33 may also or alternatively be formed in either or both of the upper or lower surfaces 42 and 43.

In one alternative embodiment, not shown, the taper angle of the distal end 32 is shallower than that shown in FIG. 3A so that the taper extends further and may extend all the way to a proximal end 50. The terms "proximal" and "distal" refer to positions along axis A-A in FIG. 3A. The slot(s) 33 can be continuous throughout the entire length of the wedge 30 or it can stop anywhere along its length for example at an abutment 34 at or near the distal end 32 of the rod 31.

FIG. 3B shows a cross-section of wedge 30 along section 3B-3B in FIG. 3A showing two slots 33a and 33b on each side of wedge 30. The cross-section has the appearance of an I-beam having two horizontal flanges, one on the top and a second on the bottom, spaced vertically by a vertical web. The wedge 30 is lumen-less and grooves or channels 33 formed on the outside surface(s) of the rod 31 are open. The grooves or channels 33 enable fluid to flow alongside the outer surface(s) of the wedge 30 and diffuse from the anterior chamber 3 into the suprachoroidal space 11, as will be described in greater detail below.

The axial length of wedge 30 measured along axis A-A from the distal end 32 to the proximal end 50 can be from 3 mm to 10 mm, and preferably 6 mm. The cross-sectional dimensions depicted on FIG. 3B are width 37 of 0.5 mm to 1 mm, and preferably 0.75 mm. The height 36 is 0.4 to 0.8 mm, and preferably 0.5 mm. The width of slots 33, denoted as 38, can be from 0.05 mm to 0.25 mm, preferably 0.15 mm. An indentation or depth 39 of slots 33 into wedge 30 are less than 40% of the width 37 of wedge 30 and can range from 0.05 mm to 0.4 mm, and preferably 0.25 mm. Although the drawings shown the leading edge of the wedge 30 at the distal end 32 as a sharp edge, the edge may have a radius of about 0.005 inch.

Although the wedge 30 is shown as an I-beam-shaped cross-section in FIG. 3B, other cross-sectional shapes can be used as exemplified in FIGS. 7 and 8. For example, FIG. 7 shows a cross section of a wedge 70 that has two lobes 70a and 70b that intersect thereby defining a set of open grooves or channels 73a and 73b on the outer surface of the wedge 70. Also, FIG. 8 shows a cross-section of a wedge 80 that has three lobes 80a, 80b, and 80c, which intersect defining a set of three open grooves or channels 83a, 83b, and 83c on the outer surface of the wedge 80.

The wedge 30 is made from any biomaterial including polyolefins such as poly(styrene-block-isobutylene-block-styrene) (SIBS), styrene ethylene butylene styrene (SEBS), polyhexene, polypropylene, polyethylene, and the like, as well as copolymers of the above. Other materials comprising the wedge 30 can include but are not limited to silicone rubber (polydimethylsiloxane and polyphenylsiloxane and copolymers thereof), polyurethane such as polyether urethane, polycarbonate urethane, polysilicone urethane, polyisobutylene urethane and other polyurethanes used for medical implantation; fluorinated polymers can also be used such as polyvinyldifluoride (PVDF) and fluorinated versions of the above. Other materials can be used for this embodiment include stiffer materials such as PEEK, polyimide, polysulfone, ridged polyurethane, polyamide, etc. Biological materials can also be used for the wedge such as crosslinked gelatin (porcine, equine, bovine, feline, etc.) crosslinked polysaccharides (gellen, pectin, hyaluronic acid, methyl cellulose, and the like). However, the preferred materials are those that are biocompatible and significantly flexible to take on the shape of the suprachoroidal space. A preferred material to be used in forming the wedge 30 is poly(styrene-block-isobutylene-block-styrene) (SIBS) of Shore 30A to 60A hardness as described in detail in U.S. Pat. Nos. 9,101,444; 9,044,301; 7,837,644; 7,594,899; and 7,431,709, herein incorporated by reference in their entireties. The wedge 30 may be extruded as a long, contoured monofilament, which can be cut to length. The extruded, cut monofilament can then be heat-formed at one end (e.g., the distal end 32) to form features (e.g., abutment 34 and taper of the distal end 32) of the wedge 30 that may have not been formed by extrusion and cutting.

Figure 4:
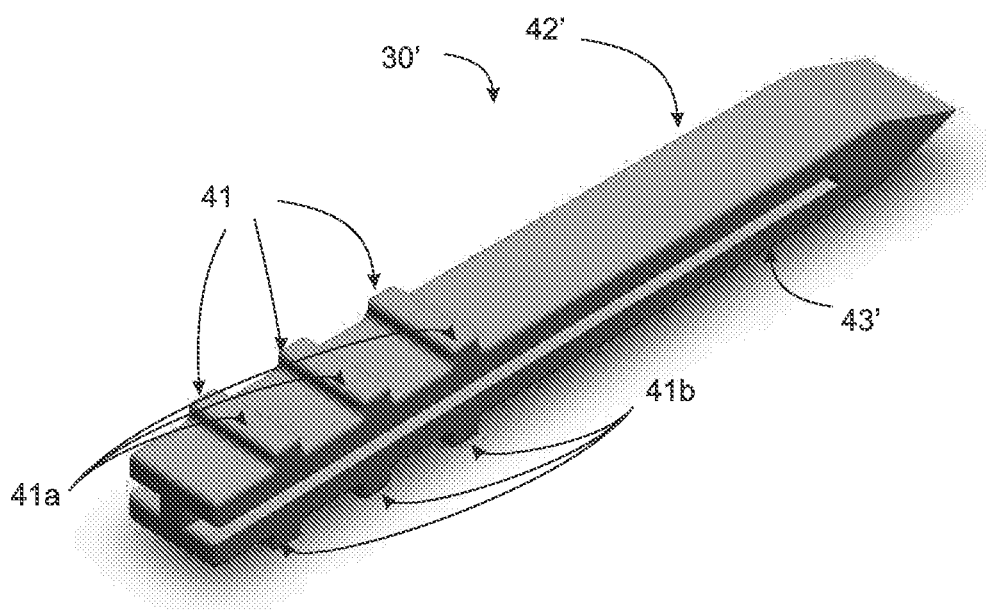
FIG. 4 is an isometric view of another embodiment of a glaucoma drainage device in accordance with this disclosure.

FIG. 4 shows another embodiment of a wedge 30' which has a plurality of barbs 41 on an upper surface 42' and on a lower surface 43'. The barbs 41 are configured to engage the tissue defining the suprachoroidal space 11 so that when the wedge 30' in introduced into the suprachoroidal space 11, the barbs 41 will help retain and fixate the wedge 30' in its implanted position and inhibit migration or ejection of the wedge 30' back out of the suprachoroidal space 11. While the barbs 41 are shown as having flat outer surfaces 41a (parallel with the upper and lower surfaces 42' and 43') in FIG. 4, the barbs can also have outer surfaces 41a that extend at non-zero angles relative to the upper and lower surfaces 42' and 43' to allow easy insertion into the suprachoroidal space 11, while resisting removal in the other direction. Although the barbs 41 are shown protruding from the surfaces of the wedge 30', the barbs 41 can also be indents, ridges, or grooves (not shown) formed in the surface.

As noted above, the wedge 30 is configured for implantation at least partly in the suprachoroidal space 11. Preferably, when in a fully implanted configuration, the distal end 32 of the wedge 30 is located in the suprachoroidal space 11 and the proximal end 50 is located in the anterior chamber 3, as shown in FIG. 5. Note that as shown in FIG. 5, the wedge 30 conforms to the curved shape of the suprachoroidal space 11, which is parallel to the curvature of the eye. In the fully implanted configuration, the wedge 30 may extend 0.5 mm to 1 mm into the anterior chamber 3. This spacing can help prevent closure of the suprachoroidal space 11 around the proximal end 50 of the wedge 30, which, if closed, would cut off the flow of fluid from the anterior chamber 3 to the suprachoroidal space 11.

FIG. 6 shows an end-view 60 (viewed from the proximal end 50 looking distally) of wedge 30 in the implanted configuration shown in FIG. 5, as seen from the anterior chamber 3 using optical coherence tomography (OTC). Insertion of wedge 30 into the suprachoroidal space 11 causes cleavage or spreading between portions of one or more of the sclera 8, choroid 10, trabecular meshwork 14, and scleral spur 20, forming a cleft 61 between the tissues and the wedge 30, which increases the size of the fluid opening between the anterior chamber 3 and the suprachoroidal space 11 to promote the flow of aqueous humor from the anterior chamber 3 into to the suprachoroidal space 11.

The wedge 30 can be implanted alone or in conjunction with one or more therapeutic agents. These therapeutic agents can be injected into the eye at the time of surgery or coated on the device or embedded within the device to elute therefrom. In addition, these therapeutic agents can be injected periodically following implantation of the wedge. Also, the wedge 30 may be formed from a biodegradable polymer matrix or coated with a biodegradable polymer matrix, where the biodegradable polymer matrix is loaded with a therapeutic agent that can be released from the matrix into the eye over time. The biodegradable polymer matrix can degrade over time in vivo (in the implanted position in the eye) and such degradation can be required to achieve the desired release rate of the therapeutic agent from the matrix into the eye over time.

In embodiments, the biodegradable polymer matrix can be selected from the group consisting of one or more biodegradable polymers in varying combinations, such as polymers, copolymers, and block polymers. Some examples of such biodegradable polymers include polyglycolides, polylactides, polycaprolactones, polyglycerol sebacate, polycarbonates e.g. tyrosine derived, biopolyesters such as poly($\beta$-hydroxyalcanoate)s (PHAs) and derived compounds, polyethylene oxide, polybutylene terepthalate, polydioxanones, hybrids, composites, collagen matrices with growth modulators, proteoglycans, glycosaminoglycans, vacuum formed SIS (small intestinal submucosa), fibers, chitin, and dextran. Any of these biodegradable polymers may be used alone or in combination with these or other biodegradable polymers in varying compositions. The biodegradable polymer matrix preferably includes biodegradable polymers such as polylactide (PLA), polyglycolic acid (PGA) polymer, poly (e-caprolactone) (PCL), polyacrylates, polymethacryates, or other copolymers. The pharmaceutical drug may be dispersed throughout the biodegradable polymeric matrix. The pharmaceutical drug may diffuse out from the biodegradable polymeric matrix to elute the drug and/or the pharmaceutical drug may separate from within the biodegradable polymer matrix and diffuse out from the biodegradable polymeric matrix to elute the drug. Examples of such a biodegradable polymer matrix are described in U.S. Pat. No. 8,685,435 (Nivaggioli et al.), the entire contents of which are incorporated herein by reference.

The therapeutic agents(s) can include anti-proliferation agents that prevent or delay cell division, for example, by inhibiting replication of DNA, and/or by inhibiting spindle fiber formation, and/or by inhibiting cell migration) or other agents that minimize fibrosis. Examples of such therapeutic agents follow.

Representative examples of therapeutic agents include the following: Visudyne, Lucentis (rhuFab V2 AMD), Combretastatin A4 Prodrug, SnET2, H8, VEGF Trap, Cand5, LS 11 (Taporfin Sodium), AdPEDF, RetinoStat, Integrin, Panzem, Retaane, Anecortave Acetate, VEGFR-1 mRNA, ARGENT cell-signalling technology, Angiotensin II Inhibitor, Accutane for Blindness, Macugen (PEGylated aptamer), PTAMD, Optrin, AK-1003, NX 1838, Antagonists of avb3 and 5, Neovastat, Eos 200-F and any other VEGF inhibitor.

Other therapeutic agents can be used such as: mitomycin C, 5-fluorouracil, dexamethasone, corticosteroids (corticosteroid triamcinolone acetonide is most common), modified toxins, methotrexate, adriamycin, radionuclides (e.g., such as disclosed in U.S. Pat. No. 4,897,255, herein incorporated by reference in its entirety), protein kinase inhibitors (including staurosporin, which is a protein kinase C inhibitor, as well as a diindolo alkaloids and stimulators of the production or activation of TGF-beta, including tamoxifen and derivatives of functional equivalents, e.g., plasmin, heparin, compounds capable of reducing the level or inactivating the lipoprotein Lp(a) or the glycoprotein apolipoprotein(a) thereof), nitric oxide releasing compounds (e.g., nitroglycerin) or analogs or functional equivalents thereof, paclitaxel or analogs or functional equivalents thereof (e.g., taxotere or an agent based on Taxol®, whose active ingredient is paclitaxel), inhibitors of specific enzymes (such as the nuclear enzyme DNA topoisomerase II and DAN polymerase, RNA polyermase, adenl guanyl cyclase), superoxide dismutase inhibitors, terminal deoxynucleotidyl-transferas, reverse transcriptase, antisense oligonucleotides that suppress cell proliferation, angiogenesis inhibitors (e.g., endostatin, angiostatin and squalamine), rapamycin or sirolimus and its derivatives such as everolimus or zoltarolimus, cerivastatin, and flavopiridol and suramin and the like.

Other examples of therapeutic agents include the following: peptidic or mimetic inhibitors, such as antagonists, agonists, or competitive or non-competitive inhibitors of cellular factors that may trigger proliferation of cells or pericytes (e.g., cytokines (for example, interleukins such as IL-1), growth factors (for example, PDGF, TGF-alpha or -beta, tumor necrosis factor, smooth muscle—and endothelial—derived growth factors such as endothelin or FGF), homing receptors (for example, for platelets or leukocytes), and extracellular matrix receptors (for example, integrins).

Still other examples of therapeutic agents include the following: subfragments of heparin, triazolopyrimidine (for example, trapidil, which is a PDGF antagonist), lovastatin, and prostaglandins E1 or I2.

FIGS. 9 to 13 show an inserter 90 that can be used to insert the wedge 30 into the suprachoroidal space 11 on one side of the eye using an ab interno approach via the clear corneal incision 13 (FIG. 1) on a diametrically opposite side of the eye. The inserter 90 includes a handle 100 (FIG. 12) that is made from a rigid material which may include medical grade polymers or metals such as polycarbonate, polypropylene, polysulfone, polyimide, polyamide, polyurethane, ABS, polymethylmethacrylate, and the like. Metals can include iron, stainless steel, nickel, titanium, gold, platinum and alloys of the above.

The inserter includes an elongated guide rod 91 that is coupled to the handle 100 and extends from a proximal end 96 at the distal end of the handle 100 to a distal end 97 spaced axially along axis A-A from the proximal end 96. Slots 93 are formed on opposite sides of the guide rod 91 and the slots may extend into the handle 100. The inserter includes rods 92 which are coupled to the handle 100 and area configured to translate in the slots 93. The rods 92 and the guide rod 91 may be formed from metal (e.g., aluminum, stainless steel, titanium) and may be planar or prebent or curved to facilitate positioning of the wedge 30 in the eye, as will be described in greater detail below. Each rod 92 has a thickness and width sufficient that they fit in and slide relative to open groove or channel 33. Also, the rods may have a width that is about the width 39 of the open groove or channel 33.

A thumb slide 94 is rigidly attached to the rods 92 within the handle 100 and the thumb slide 94 is configured to translate with the rods 92. Specifically, the handle defines a slot 95 in which the thumb slide 94 translates. The handle 100, slots 95 and 93, and rods 92 extend parallel to axis A-A. Translational movement of the thumb slide 94 in the slot 95 causes corresponding movement of the rods 92 in their slots 93. The rods 92 can be positioned between an extended position shown in FIGS. 9 and 11, in which the thumb slide 94 is moved toward a distal end of the slot 95, and a retracted configuration as shown in FIG. 10, in which the thumb slide 94 is moved towards an opposite, proximal end of the slot 95. The movement of the thumb slide 94 and the rods 92 may be used to implant the wedge 30 in the suprachoroidal space 11 as described in greater detail below.

In one embodiment, the inserter 90 functions as follows. The inserter 90 and the wedge 30 are coupled together, as shown, for example, in FIG. 11. The slots 93 of the extension rod 93 are configured to align with open grooves or slots 33 of the wedge 30 so that rods 92 may span slots 33 and 93 in the extended configuration to couple the wedge 30 to the inserter 90, as shown in FIGS. 11 and 12. Looking at FIG. 11, rods 92 of inserter 90 are received in slots 33a and 33b of wedge 30 such that distal ends 92a (FIG. 9) of the rods 92 engage the abutment 34 of wedge 30. When the wedge 30 is coupled to the inserter 90, the proximal end 50 of the wedge 30 engages or otherwise abuts the distal end 97 of the extension rod 91. The wedge 30 may be pre-assembled with the inserter 90 and provided to a user as a kit.

With the wedge 30 coupled to the inserter 90 as shown in FIG. 11, the user holds the inserter 90 while introducing the distal end 32 of the wedge 30 first into the clear corneal incision 13 with the use of a gonioscope (not shown) as well as a viscous fluid (not shown) in the anterior chamber 3 to maintain it open. After the wedge 30 is introduced into the eye, the distal end 97 of the extension rod 91 follows the wedge 30 and is introduced into the eye. The axial length of the extension rod 91 is sufficient that the handle 100 remains outside of the eye at all times during use of the inserter 90. The width and height of the extension rod 91 are preferably equal to or less than the width 37 and height 36 of the wedge 30 so that the extension rod 91 does not enlarge the pathway through the eye caused by the positioning of the wedge 30 during its implantation.

The distal end 32 of the wedge 30 is pushed by at least one of the extension rod 91 and the rods 92 and advanced diametrically across the anterior chamber 3 from the corneal incision 13 towards the scleral spur 20. The distal end 32 of the wedge 30 is advanced through the trabecular meshwork 14, and between the interface of the scleral spur 20 and the ciliary body, and finally into the suprachoroidal space 11 (just to the left of it in FIG. 5). When crossing the anterior chamber 3, it may be useful to maintain the plane of the upper and lower surfaces 42 and 43 of the wedge 30 parallel to the plane of the iris. By pushing the ends 92a of the rods 92 against abutment 34 and/or by pushing the distal end 97 of the extension rod 91 against the proximal end 50 of the wedge 30, the wedge 30 can be pushed into suprachoroidal space 11. Once the wedge 30 is in the fully implanted configuration shown in FIG. 5, the thumb slide 94 can be retracted proximally in slot 95, which also retracts the rods 92 proximally from the grooves 33a and 33b. Once the rods 92 are fully clear of the proximal end 50 of the wedge 30, the extension rod 91 of the inserter 90 can be retracted from the eye, leaving the wedge 30 implanted in the eye in the implanted configuration shown in FIG. 5.

In one embodiment, the inserter 90 includes a spring or other actuation mechanism to automatically retract the thumb slide 94 from the extended position when the thumb slide 94 is pressed (i.e., pressed downwardly in FIG. 11). In addition, in one embodiment, the inserter 90 may include a lock mechanism configured lock the position of the thumb slide 94 in the extended configuration shown in FIG. 11 to prevent inadvertent deployment or decoupling of the wedge 90. The inserter handle 100 can be grasped and held in a user's hand so that the user's thumb can actuate the thumb slide 94. Portions of the rods 92 can have dimensions that are larger than the dimensions of the slots 33 (i.e., they can have a radially outer portion that is outside the grooves 33). For example, the rods may have a "T" shaped cross-section and have an outer beam portion that extends along a plane perpendicular to the portion of the rods received in the slots 33. The outer beam portion may have dimensions larger than those of the slots 33 to provide the rods 92 more columnar strength (slots 33 will flex larger).

FIG. 13 shows another alternate embodiment of the inserter 90 and the wedge 30 in which a wedge 30" is formed like wedge 30 but does not have abutments 34 and in which ends 92a" are formed with sharp cutting surfaces that extend distally of the distal end 32" of the wedge 30". When the distal end of the extension rod 91" pushes against the proximal end 50" of the wedge 30" in the eye, the sharp cutting surfaces of ends 92a" can facilitate cutting tissue ahead of the inclined surfaces at the distal end 32" of the wedge 30".

There have been described and illustrated herein several embodiments of an ocular wedge implant and a method of implantation of the wedge implant. While particular embodiments of the implant and method have been described, it is not intended that the invention be limited thereto, as it is intended that the invention be as broad in scope as the art will allow and that the specification be read likewise. Thus, while particular wedge implants have been disclosed, it will be appreciated that other wedge implant may be used as well. In addition, while particular types of materials have been disclosed for the composition of the wedge, it will be understood that other materials with the same material properties can be used. Also, while the use of an inserter to implant the wedge is preferred, it will be recognized that the wedge may be inserted and implanted without any specific inserter. It will therefore be appreciated by those skilled in the art that yet other modifications could be made to the provided invention without deviating from its spirit and scope as claimed.

What is claimed is:

1. A glaucoma drainage device, the device comprising:
a lumen-less elongated body extending axially from a tapered distal end to a proximal end, the tapered distal end formed as a wedge with a leading distal edge, the body having opposed upper and lower flat outer surfaces and at least one outer surface that defines at least one open groove extending from at or near the proximal end towards the tapered distal end of the body, the open groove formed as an indentation in an outer surface of the body and disposed between the opposed upper and lower flat outer surfaces of the body,
wherein the elongated body is configured to lodge in the suprachoroidal space of an eye and extend into the anterior chamber of the eye to permit aqueous humor from the anterior chamber of the eye to flow along the open groove from the anterior chamber of the eye to the suprachoroidal space of the eye, and
wherein the open groove terminates at an abutment defined by the elongated body, the abutment being disposed at a distal end of the open groove, and the abutment being spaced proximally from the tapered distal end of the body.

2. The device according to claim 1, wherein:
the body defines a plurality of open grooves that extend parallel to one another from the proximal end towards the tapered distal end of the body, wherein the plurality of open grooves are formed as indentations in outer surfaces of the body and disposed between the opposed upper and lower flat outer surfaces of the body and terminate at corresponding abutments defined by the elongated body, the abutments being spaced proximally from the tapered distal end.

3. The device according to claim 1, wherein:
the body is formed of a material having a hardness of Shore 30A to 60A.

4. The device according to claim 3, wherein:
the body is formed of at least one of poly(styrene-block-isobutylene-block-styrene) (SIBS), styrene ethylene butylene styrene (SEBS), polyhexene, polypropylene, and polyethylene.

5. A glaucoma device kit comprising:
a glaucoma drainage device including a lumen-less elongated body extending axially from a tapered distal end to a proximal end, the distal end formed as a wedge with a leading distal edge, the body having opposed upper and lower flat outer surfaces and at least one outer surface that defines at least one open groove extending from at or near the proximal end towards the distal end of the body, the open groove formed as an indentation in an outer surface of the body and disposed between the opposed upper and lower flat outer surfaces of the body,
wherein the elongated body is configured to lodge in the suprachoroidal space of an eye and extend into the anterior chamber of the eye to permit aqueous humor from the anterior chamber of the eye to flow along the open groove from the anterior chamber of the eye to the suprachoroidal space of the eye, and
wherein the open groove terminates at an abutment defined by the elongated body, the abutment being disposed at a distal end of the open groove, and the abutment being spaced proximally from the tapered distal end of the body; and
an inserter coupled to the glaucoma drainage device, the inserter configured to deliver and position the glaucoma drainage device in the suprachoroidal space and to decouple from the glaucoma drainage device to deploy the glaucoma drainage device in the suprachoroidal space.

6. The kit according to claim 5, wherein:
the inserter includes a handle and at least one rod configured for longitudinal translation relative to the handle, the at least one rod being configured for longitudinal translation in the at least one open groove of the body of the glaucoma drainage device, wherein the at least one rod has an extended configuration in which the rod is located in a portion of the open groove and engages the abutment defined by the body of the glaucoma drainage device.

7. The kit according to claim 6, wherein:
the inserter is configured to decouple from the glaucoma drainage device by reconfiguring the at least one rod from the extended configuration to a retracted configuration in which the rod is not located in a portion of the open groove of the glaucoma drainage device.

8. The kit according to claim 7, wherein:
the at least one rod is coupled to a slide member configured for actuation by a user's hand, the inserter handle defining a longitudinal slot extending axially along the length of the handle and parallel with the at least one rod, wherein the slide member is configured to slide within the slot to move the rod between the extended and retracted configurations.

9. A method of implanting a glaucoma drainage device, the method comprising:
providing a glaucoma drainage device including a lumenless elongated body extending axially from a tapered distal end to a proximal end, the tapered distal end formed as a wedge with a leading distal edge, the body having opposed upper and lower flat outer surfaces and at least one outer surface that defines at least one open groove extending from at or near the proximal end towards the distal end of the body, the open groove formed as an indentation in an outer surface of the body and disposed between the opposed upper and lower flat outer surfaces of the body, wherein the elongated body is configured to lodge in the suprachoroidal space of an eye and extend into the anterior chamber of the eye to permit aqueous humor from the anterior chamber of the eye to flow along the open groove from the anterior chamber of the eye to the suprachoroidal space of the eye, and wherein the open groove terminates at an abutment defined by the elongated body, the abutment being disposed at a distal end of the open groove, and the abutment being spaced proximally from the tapered distal end of the body;
providing an inserter coupled to the glaucoma drainage device, the inserter having a handle configured to be grasped by a user and at least one rod configured for longitudinal translation relative to the handle in the at least one open groove, wherein the at least one rod has an extended configuration in which the rod is located in a portion of the open groove and engages the abutment defined by the elongated body, the inserter configured to deliver and position the glaucoma drainage device in the suprachoroidal space and to decouple from the glaucoma drainage device to deploy the glaucoma drainage device in the suprachoroidal space;
introducing the ocular glaucoma drainage device into the eye while maintaining the handle outside of the eye;
positioning the glaucoma drainage device at a desired implanted position in the suprachoroidal space;
with the glaucoma drainage device positioned at the desired implanted position, decoupling the inserter from the glaucoma drainage device.

10. The method according to claim 9, wherein
positioning the glaucoma drainage device at a desired implanted position in the suprachoroidal space includes positioning the distal end of the glaucoma drainage device in the suprachoroidal space and positioning the proximal end of the glaucoma drainage device in the anterior chamber.

11. The method according to claim 10, wherein:
at the desired position, the glaucoma drainage device extends about 0.5 mm to 1 mm into the anterior chamber.

12. The method according to claim 9, wherein:
the inserter is configured to decouple from the glaucoma drainage device by reconfiguring the at least one rod from the extended configuration to a retracted configuration in which the rod is not located in a portion of the open groove of the body of the glaucoma drainage device, and
wherein decoupling the inserter from the glaucoma drainage device includes reconfiguring the at least one rod from the extended configuration to the retracted configuration.

13. The method according to claim 12, wherein:
the at least one rod is coupled to a slide member configured for actuation by the user's hand, the inserter handle defining a longitudinal slot extending axially along the length of the handle and parallel with the at least one rod, wherein the slide member is configured to slide within the slot to move the rod between the extended and retracted configurations.

14. The device according to claim 1, wherein:
the at least one groove is defined by opposed sidewalls that extend from an opening, the opposed sidewalls being joined by a floor disposed opposite the opening.

15. The device according to claim 1, wherein:
the at least one open groove comprises two open grooves that extend parallel to one another from the proximal end towards the tapered distal end of the body, wherein the two open grooves are disposed between the opposed upper and lower flat outer surfaces of the body and terminate at corresponding abutments defined by the elongated body, the abutments being spaced proximally from the tapered distal end.

16. The device according to claim 15, wherein:
the two open grooves are disposed on opposite sides of the longitudinal axis of the body.

* * * * *